ns*

United States Patent [19]

McNeil et al.

[11] Patent Number: 5,403,549
[45] Date of Patent: Apr. 4, 1995

[54] METHOD FOR STERILIZATION USING A FLUID CHEMICAL BIOCIDE

[75] Inventors: Frank P. McNeil; Christopher G. Anderson; Larry A. Gaudioso, all of Salt Lake City, Utah

[73] Assignee: CYCLO₃PSS Medical Systems, Inc., Salt Lake City, Utah

[21] Appl. No.: 148,829

[22] Filed: Nov. 4, 1993

[51] Int. Cl.⁶ ............................................. A61L 2/18
[52] U.S. Cl. ................................ 422/29; 422/28; 422/1; 422/32
[58] Field of Search ................... 422/28, 29, 32, 36

[56] References Cited

U.S. PATENT DOCUMENTS 4,376,094 3/1983 Münzenmaier et al. ............... 422/36
5,021,182 6/1991 Jentsch ................................... 422/28

*Primary Examiner*—Robert J. Warden
*Assistant Examiner*—T. A. Trembley
*Attorney, Agent, or Firm*—Thorpe, North & Western

[57] ABSTRACT

A method and a composition for disinfecting matter or materials such as medical instruments, operating rooms, examining tables, walls, windows, floors, solutions, porous substances and the like contaminated with bacteria, bacterial spores, fungi, or viruses is disclosed. The composition consists of a mixture of a peroxymonosulfate and a carbonyl-containing compound and reaction products thereof and is preferably dioxirane formed by in situ oxidation of a ketone or aldehyde by the peroxymonosulfate in aqueous solution. Carbonyl-containing compounds that have been tested include acetone, 2-pentanone, 4-hydroxy-4-methyl-2-pentanone, and camphorsulfonic acid. The method includes providing a solution containing the dioxirane reaction mixture and contacting the matter or materials with it at room temperature for a time sufficient to disinfect and sterilize the matter or materials.

27 Claims, No Drawings

METHOD FOR STERILIZATION USING A FLUID CHEMICAL BIOCIDE

BACKGROUND OF THE INVENTION

1. Field of the Invention

This invention relates to a composition and method for disinfecting and sterilizing matter contaminated with bacteria, fungi, spores, viruses, and the like.

2. Perspective of the Invention

Institutions such as hospitals, clinics, physicians, biomedical laboratories, food processors, and pharmaceutical and cosmetic industries all utilize liquid sterilization or disinfection methods. The invention is directed to a method for disinfecting and sterilizing various forms of matter where an effective sterilant or disinfectant is needed. Such matter may include medical instruments, examining tables, glassware, doors, windows, walls, solutions, enclosed spaces or chambers such as incubators, laboratory equipment, and the like. Therefore, the invention has potential application for use in all of the above fields and other fields where an effective sterilant or disinfectant is needed. For purposes of illustration only, medical instruments will be exemplified throughout this description.

Medical instrument sterilization procedures provide for the inactivation of infectious microorganisms and are of particular importance in the disinfection and sterilization of reusable and certain disposable medical instruments and devices, implantable devices, and prosthetics. Effective sterilization of these items and equipment for manufacturing medical products is essential. The ongoing AIDS, concomitant tuberculosis (TB), and Hepatitis B epidemics underscore the need for effective broad spectrum appliance sterilization. Patient-to-patient transmission of microbial diseases through contaminated instruments and devices has been reported. Weller, I. et al., 29 *Gut* 1134 (1988); Hanson, P. & Collins, J., 44 *Thorax* 778 (1989); Bond, W., 257 *J. Am. Med. Ass'n* 843 (1987). Such studies have shown the occurrence of diverse infectious agents in medical devices, particularly of HIV in fiberoptic bronchoscopes. These studies indicate a possible cause of nosocomial infections is inadequately sterilized medical devices that undergo multiple uses. Favero, M. & Bond, W., Sterilization, Disinfection, and Antisepsis in the Hospital, *Manual of Clinical Microbiology* 183–200 (American Society of Microbiology, 1989).

Pathogenic infections and the resulting complications due to contaminated devices are difficult to ascertain. The data tend to be under-reported because of long incubation times and removal of patients from the exposure site. Incidences of infection of 6% for pneumonia, 30% for bacteriemia, and 46% for fever after bronchoscopies have been shown. Pereira, W., et al., 112 *Am. Rev. Resp. Dis.* 59 (1975); Burman, S., 40 *J. Thoracic and Cardiovas. Surg.* 635 (1960). Although bronchoscope contamination seems to be the best documented, several other medical devices have also been related to transmission of disease. Transmission of hepatitis by contaminated medical devices has long been a concern of surgeons and clinicians. Bacterial contamination inside a spirometer after one week's use has been measured at one-hundred million ($10^8$) organisms per milliliter. Houston et al., 12 Breath 10 (1981). Some models of ventilators and respirators are also suspect in the transmission of infectious microorganisms.

Sterilization procedures are necessarily directed toward the destruction of ubiquitous microbes. Some bacterial spores are extremely resistant to heat and require heating in steam under pressure at greater than 120° C. for as long as eleven hours to insure destruction. Most spores are not this resistant, however, and are killed by moist heat at greater than 120° C. for thirty minutes. Bacterial spores are also very resistant to bactericidal compounds. For many commonly used disinfectants, such as hypochlorite and phenols, concentrations one-thousand to ten-thousand times greater are needed to kill spores than are needed to kill vegetative cells. An exception to this generalization is alkalating agents, such as ethylene oxide or formaldehyde, where one-half to fifteen times as much alkalating agent is needed to kill spores than is needed to kill vegetative cells. Therefore, a sporicidal agent that is capable of sterilizing a wide range of medical devices and instruments in a simple and straight forward fashion is desirable.

Prior Art

Dioxiranes are a comparatively new class of compounds. The attempted isolation of dioxiranes began in 1974 when Montgomery observed that ketones enhance the rate of decomposition of peroxymonosulfate salts (also known as caroate), with several oxidation reactions of caroate shown to be catalyzed by ketones. Montgomery, R., 96 *J. Am. Chem. Soc.* 7820 (1974). It was then proposed that a variety of ketones could enhance caroate decomposition leading to a theoretical, general class of compounds called dioxiranes. The proposed reaction scheme is as follows:

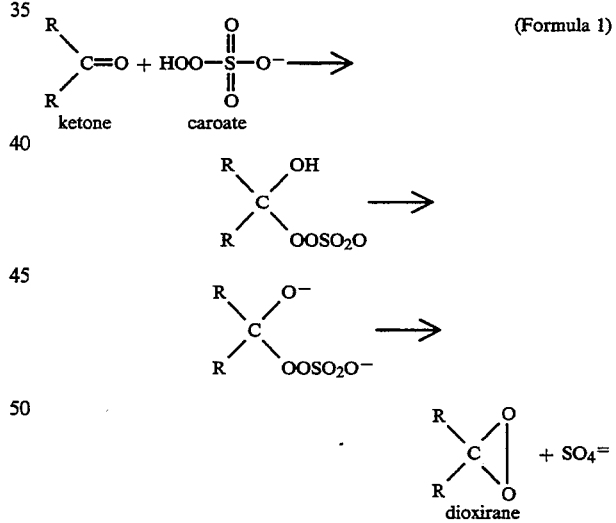

Confirmation of the dioxiranes as a new class of compounds was obtained by Murray and co-workers when they isolated dimethyldioxirane (DMD) (R=CH$_3$ in Formula I) in 1985. Murray, R. & Jeyaraman, R., 50 *J. Org. Chem.* 2847 (1985). The preparation of dimethyldioxirane from the corresponding ketone (acetone) and caroate (KHSO$_5$) has provided convenient access to a series of powerful oxidants. Murray, R. & Jeyaraman, R., 50 *J. Org. Chem.* 2847 (1985).

The in situ preparation of some dioxiranes is accomplished by adding caroate (peroxymonosulfate) to solutions of a variety of ketones. Alternatively, some dioxiranes can be generated and purified via distillation to yield dilute solutions in the ketone from which they were prepared, for example dimethyldioxirane in acetone.

The preparation of dimethyldioxirane from the corresponding ketone (acetone) and caroate (KHSO$_5$) proceeds as follows:

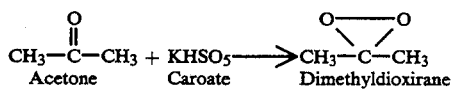

and methyl-n-propyldioxirane is formed from 2-pentanone;

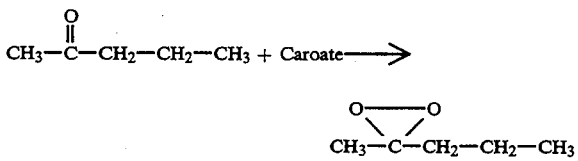

The following examples are illustrative of the potent, yet specific, oxidative properties of dioxiranes. U.S. Pat. No. 5,087,752 issued to Murray et al. sets out a process for the synthesis of nitroxides utilizing dioxiranes. This patent discusses prior methods of synthesizing nitroxides from secondary amines, which were replete with problems such as the lack of significant yields and the generation of unwanted by-products. These problems effectively negate the value of such earlier methods. Contrasted thereto, the Murray method provides a general procedure for synthesizing nitroxides from secondary amines that is simple, can be conducted in a single reaction vessel with high yields, and produces few or no unwanted by-products. The reaction proceeds as follows:

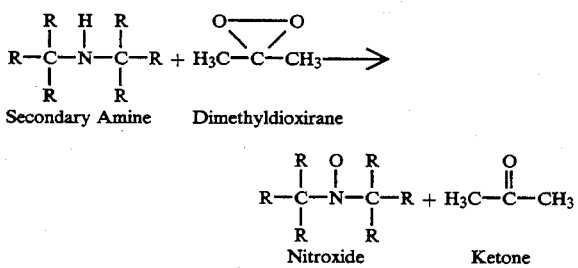

The Murray process provides for the production of nitroxides by reacting a secondary amine with two molar equivalents of a dioxirane. The secondary amine is initially oxidized to a hydroxylamine intermediate which is further oxidized to form the nitroxide. In later work, Murray, et al. also generated dimethyldioxirane (DMD) using a caroate (peroxymonosulfate)-acetone system for the production of epoxides from alkenes, conversion of acetaldehyde to acetic acid and norbornene to the epoxide. R. Murray, 89 *Chem. Rev.* 1187 (1989). Also, Edwards, et al. used a peroxymonosulfate-acetone system to provide for stereospecific epoxidation of alkenes. Edwards, J. et al., 22 *Acc. Chem. Res.* 205 (1989). Additionally, similar processes have been used to convert pyridine to pyridine oxide and phenylmethylsulfide to phenylmethylsulfoxide, and finally, acetone diperoxide and triperoxide were generated at 52° C. within 16 hours in excess caroate.

Murray and Jeyaraman, *J. Org. Chem.*, 50, 2847 (1985), further reported that in situ prepared solutions of dioxirane at room temperature reacted with substances in solution to give high yields of specific products, for example: (A) Ethyl trans-cinnamate, cis-stilbene, and trans-stilbene were all converted to the corresponding epoxides in 75 to 95% yield (GLPC determinations). In all cases the reactions were stereospecific with retention of configuration. (B) Phenanthrene was converted to its 9, 10-oxide (83% yield) and phenylmethylsulfide was converted to phenylmethylsulfoxide (84% yield). (C) 2-butanone was converted to ethylmethyldioxirane and that solution was used to convert phenanthrene to its 9, 10-oxide (82% yield) and trans-stilbene to trans-stilbene oxide (58% yield).

Following the lead of Murray and Jeyaramans, Curci et al., 30 *Photochem. & Photobiol.* 63 (1979), clarified the chemistry of dioxirane formation by postulating the existence of "carbonyl oxides" as key intermediates in a number of oxidation processes. The dioxiranes are members of the smallest cyclic peroxide system, and are isomeric with the carbonyl oxides, Lovas, F. & Suenram, R., 51 *Chemical Physical Letters* 453 (1977); Adam, W. et al., 22 *Acc. Chem. Res.* 205 (1989), one of the peroxidic intermediates involved in the ozonolysis process. Current evidence suggests the possible involvement of carbonyl oxides in dioxirane chemistry.

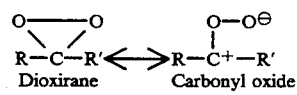

Dioxirane (H$_2$CO$_2$) produced by ozonolysis of ethylene is not stable, but has been characterized by spectral and microwave methods. Adam, W. et al., 22 *Acc. Chem. Res.* 205 (1989); Suenram, R. & Lovas, F., 100 *J. Am. Chem. Soc.* 5117 (1978).

While dioxiranes have been utilized as intermediates for the preparation of other compounds no biological activity or utility has been demonstrated.

The use of aqueous solutions of potassium peroxymonosulfate as a biocide against certain bacteria and fungi is disclosed in U.S. Pat. No. 3,873,696. Also, the virucidal use of dilute aqueous solutions of potassium peroxymonosulfate is claimed in U.S. Pat. No. 4,404,191.

A wide spectrum disinfectant, alleged to be effective against bacteria, fungi, viruses, and bacterial and fungi spores is taught in U.S. Pat. No. 5,186,946 and consists of up to 90% by weight of potassium peroxymonosulfate along with balanced ratios of malic and sulfamic acids. In addition, a chelating agent such as a sodium salt of EDTA and a detergent consisting of an alkylated ether of polyethylene glycol are each required. These are stated to function in a synergistic manner and provide the production of hydrogen peroxide and oxygen, as the active ingredients. This is accomplished by the decomposition of the potassium monoperoxysulfate, triggered by the irreducible malic and sulfamic acids. One mode of biocidal action is stated to be the disruption of disulfide bonds in the protein coat of the spores.

It is known that disulfide bridges are a feature of cellular walls and other protein-containing features of bacterial cells. Mahler, H. & Coredes, E., Structural Organization of Proteins, *Biological Chemistry* 74 (1966). The rupture or breaking of a disulfide bridge by oxidation to sulfonic acid moieties is shown in following Formula 2:

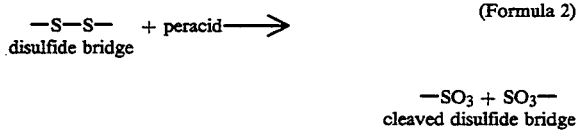

(Formula 2)

A typical bacterial spore is surrounded by an exosporium, a loose sac peculiar to some spore species. Other layers, working inwardly, include (a) multi-layered coats containing proteins rich in disulfide linkages, (b) a thick cortex layer which contains the polymer murein (or peptidoglycan), (c) a plasma membrane, and (d) a core or spore protoplasm.

A bacterial spore's first line of resistance to exogenous agents consists of the proteinaceous outer coats that contain keratin-like proteins. As is well-known, the stability of keratin structures is due to frequent primary valence cross links (disulfide bonds) and secondary valence cross links (hydrogen bonds) between neighboring polypeptide chains. Keratin-like proteins are typically insoluble in aqueous salt solutions or dilute acid or base solutions, and are also resistant to proteolytic enzymes and hydrolysis. In other words, the layered outer coats are rather inert and play a predominant role in protecting the spore against exogenous agents.

The outer layers are coats of an alkali soluble protein that tends to form fibrils in vitro. This alkali soluble layer can be removed only after mechanical rupture of the spores or treatment with a reagent that breaks disulfide bonds, such as mercaptoethanol. It has been speculated that a disulfide-rich layer holds the alkali soluble layer within the spore in some manner (the physical structure of disulfide bridges for instance could be the integral part of that cell layer function).

Penetration of the outer layers seems to play an important role in cidal action of spores. Physical or chemical modifications to the cell wall allow diffusion of anti-microbial agents into the protoplasm, thereby interrupting cellular metabolism and DNA synthesis.

The protective outer layers of bacterial vegetative cells are more susceptible to antimicrobial agents than are spores, thus an agent capable of disrupting spore cell walls and penetrating the inner layers of a spore is expected to kill vegetative cells also. Fungal cell walls vary greatly among taxa and also among vegetative and resting structures. The resistance of resting structures to antimicrobial compounds is roughly comparable to that of bacterial spores. Viruses are nucleic acids covered by a protective protein shell. Viruses are typically much more susceptible to protein disrupting agents than are bacteria and fungi.

It would be desirable to provide a broad spectrum biocide that functions effectively as a disinfectant and sterilant, which does not require the concoction of a multitude of ingredients, which does not possess residual activity over a long period of time and which does not require removal from the material or matter that has been treated.

Objects and Summary of the Invention

It is therefore a principal object of the present invention to provide a disinfectant or sterilant composition comprising a fluid mixture containing a peroxymonosulfate salt and a carbonyl-containing compound and reaction products thereof, particularly where the reaction products result in a dioxirane for inactivating viruses, fungi, and bacterial vegetative cells and spores in or on various types of matter.

It is also an object of the invention to provide a method for utilizing the disinfectant or sterilant composition such that when applied to the matter or material to be treated, under appropriate environmental conditions, the composition will act as a highly effective microbicidal agent for inactivating a broad variety of microorganisms.

Another object of the invention is to provide a disinfectant or sterilant composition consisting of a fluid mixture containing a peroxymonosulfate salt and a carbonyl-containing compound and reaction products thereof wherein the carbonyl-containing compound is a ketone or aldehyde and is particularly selected from the group consisting of acetone, 2-pentanone, 4-hydroxy-4-methyl-2-pentanone, and camphorsulfonic acid alone or in combination with one or more members selected from the group consisting of peroxides, aldehydes, epoxides and surfactants. Certain metallic ions, such as $Cu^{2+}$ may also be present.

It is another object of the invention to provide a disinfectant or sterilant composition consisting of a fluid mixture containing a dioxirane such as, but not limited to, dimethyldioxirane, 4-hydroxy-4-methyl-2-pentadioxirane, 2-pentadioxirane, and the dioxirane of camphorsulfonic acid alone or in combination with one or more members selected from the group consisting of peroxides, aldehydes, epoxides, surfactants. If desired metallic ions, such as $Cu^{2+}$ may also be present.

It is still another object of the invention to provide a disinfectant or sterilant composition comprising a fluid mixture containing a peroxymonosulfate salt and a carbonyl-containing compound and reaction products thereof, wherein at least one of the reaction products is a dioxirane that will destroy essentially all active viruses, fungi, and bacterial vegetative cells and spores commonly encountered in medical instrument sterilization operations.

It is yet another object of the present invention to provide a disinfectant or sterilant composition comprising a fluid mixture containing a peroxymonosulfate salt and a carbonyl-containing compound and reaction products thereof, wherein at least one of the reaction products is a dioxirane for use in disinfecting or sterilizing laboratory equipment, medical and prosthetic devises, homografts and heterografts, synthetic grafts, implants, food products, and the like, for use on or in the human body or environs that may be habitat for humans by treating same with said disinfectant or sterilant compositions.

These and other objects are realized in a composition containing an effective amount of a fluid mixture containing peroxymonosulfate and a carbonyl-containing compound and reaction products thereof for use as a sterilant and disinfectant for inactivating viruses, fungi, and bacterial vegetative cells and spores, as well as for inactivating select cells.

Along with the fluid mixture, other compounds may also be present as a result of reaction between the peroxymonosulfate and carbonyl-containing compound, such as dioxiranes, carbonyl oxides, epoxides, di-peroxides and possibly tri-peroxides. These other compounds may contribute to the effectiveness of the fluid mixture as a sterilant, disinfectant, microbicide and cell inhibitor. To provide a fluid mixture that functions as an effective sterilant, disinfectant, microbicide or selective cell inactivator, depends upon the selection of an appropriate ketone or aldehyde as the carbonyl-containing molecule to be combined with the proper amount of peroxymonosulfate or caroate. While it is believed that the ketone or aldehyde moiety in admixture with the caroate reacts in situ to produce dioxiranes, it cannot be discounted that the mixture per se also possesses biocidal activity.

DETAILED DESCRIPTION OF THE INVENTION

An ideal microbiocidal oxidant would be one that is efficient in transferring oxygen, is selective in its reactivity, is mild toward the oxidized product, is conveniently prepared from commercially available materials, possesses catalytic activity, and is recyclable and environmentally agreeable. The characteristics of certain fluid mixtures of peroxymonosulfate and a carbonyl-containing compound selected from the group consisting of ketones and aldehydes come close to this ideal when utilized in the manner claimed herein.

To alter the multilayered outer coats of bacterial spores and thus allow further penetration and possible interactions in the critical cortex or protoplast regions by an antimicrobial agent, one must choose a very active agent. The agents described in the present invention are ideal vehicles to provide reactive atoms, free radicals, and molecules which will drastically alter the protective layers of bacterial vegetative cells and spores, viruses, and fungi.

A desirable aspect of the invention is a process for the in situ reaction of peroxymonosulfate with ketones or aldhydes to produce fluid mixtures that are active microbicidal agents, and the use of these compounds to attack and alter the protective layers of bacterial vegetative cells and spores, fungi, and viruses, thus killing them. It is believed that mixing peroxymonosulfate with a ketone or adlehyde as a carbonyl-containing compound causes oxidation of the carbonyl-containing compound to produce a dioxirane, and possibly other compounds, that exhibit the microbicidal activity. Production of dioxiranes under the conditions described herein has not been rigorously proven, however. Although in situ preparation of the fluid mixture has given the best results and is a preferred method of practicing the invention, fluid mixtures that have previously been prepared and have sufficient shelf life are also useful in the present invention.

Specifically, as set out below and supported with the test data in the examples, the biocides utilized in the invention are shown to inactivate essentially 100% of microorganisms tested, including bacteria, bacterial spores, viruses and fungi, with an exposure to an effective amount of the fluid mixture for a sufficient amount of time. Relative to microbe destruction, the examples illustrate the conditions and successes the biocidal fluid mixtures of the invention have achieved.

As used herein, the term "biocidal fluid mixture", "caroate/carbonyl product", "carbonyl/caroate product", "fluid mixture containing a peroxymonosulfate salt and a carbonyl-containing compound and reaction products thereof", "peroxymonosulfate/carbonyl reaction product" and "dioxirane" and any other similar terms are used interchangeably. While it is believed that the biocidal properties of the fluid illustrated are attributed to the formation of dioxiranes, it is not to be disclaimed or discredited that mixtures of carbonyl-containing compounds and caroate also possess biocidal activity. The term "dioxirane" is used preferentially in describing the invention, but is deemed to be inclusive of carbonyl/caroate mixtures yielding carbonyl/caroate products. This definition is deemed to be proper because much of the dioxirane produced is by the in situ reaction of the carbonyl compound and the caroate.

As used herein, the term "carbonyl compound" means a ketone or aldehyde, and it not intended to include other compounds containing a carbonyl group, such as acids, esters, anhydrides, amides, and acyl halides. Preferably, the carbonyl compound is a ketone.

As used herein "caroate", "catoate salt", "peroxymonosulfate", "peroxymonosulfate salt" are used interchangeably and, unless otherwise stated, refer to the potassium salt and therefore are also synonymous with the terms "potassium caroate" and "potassium peroxymonosulfate."

As used herein, "matter" or "material" refers to a contaminated product which is to be sterilized or disinfected. It will preferably be a surface of some sort, such as a medical instrument, examination table, operation room tables and equipment, laboratory glassware or other surfaces, walls, doors, floors, windows, and like which require washing or wiping with a disinfectant solution. However, incubation chambers, airways, enclosed spaces, and the like may be treated with a gaseous or liquid dioxirane solution. It is further contemplated that solutions, porous materials such as sponges, foodstuffs, and any other products which can be brought into contact with the dioxirane may also be considered "matter" or "material." Hence, these terms are to be given the broadest possible definition limited only by the functionality of the caroate/carbonyl product or dioxirane in disinfecting or sterilizing such "matter" or "material."

As used herein, "medical instrument" means an instrument, implement, tool, machine, device, implantable device, prosthetic, and the like that is subject to contamination by microbes and that should be disinfected or sterilized before being used.

As used herein, "in situ" means preparing the caroate/carbonyl product or dioxirane-containing fluid mixture at or near the time and place that the fluid mixture is to be used for disinfecting or sterilizing a material.

As used herein "fluid" refers to both liquids and gases which serve as carriers for the dioxirane (caroate/carbonyl) product.

As used herein, "effective amount" means an amount of the fluid mixture containing a dioxirane or caroate/carbonyl product, and, optionally, other ingredients that are effective in killing all or virtually all of the microbes contaminating the material that is to be disinfected or sterilized within a certain time. It should be recognized that an effective amount is a function of concentration of the active ingredients of the fluid mixture and the time of exposure. As will be shown in the examples, concentrations of a fluid mixture that do not kill all contaminating microbes in a short time period are completely effective in killing all of the contaminating microbes in a longer time period. The present invention is contemplated as encompassing circumstances in which high concentrations and short times are used as well as lower concentrations and longer times.

The invention encompasses a disinfectant fluid mixture, that may be a solution or gas or a mixture thereof, prepared by mixing various ketones or aldehydes with caroate in an appropriate polar solution or gaseous environment. Preferably the polar solution is an aqueous solution but can also contain or consist of alcohols, ketones and the like. As will be shown below, it is often desirable to have an excess of caroate present. In such situations, aqueous or alcohol solutions would be preferred over a carbonyl containing solvent such as a ketone. As stated previously, it is believed that the caroate oxidizes the carbonyl moiety to form a dioxirane, and that it is the dioxirane that is the principal microbicide. For example, 2-pentanone may be mixed with caroate in water or aqueous solutions also containing other solvents or ingredients to form methyl-n-propyldioxirane. Similarly, acetone is mixed with caroate in an aqueous environment to form dimethyldioxirane. Also, camphorsulfonic acid is mixed with caroate in water to form the dioxirane of camphorsulfonic acid. All of these reactions are performed at room temperature, about 20°-25° C. The invention is not intended to be limited to the specific dioxirane or carbonyl/caroate products illustrated by the examples. In general the resulting solutions are at least about 60% water. The solutions are then ready for use to disinfect, sanitize, or sterilize surfaces or objects. However, other concentrations of caroate, ketones or aldehydes and dioxiranes may be made by dilution or concentration of the initial reaction solution. The biocidal activity of the solutions is exposure time dependent and even in low concentrations, e.g. 2.5% (w/w) caroate with 5% (w/w) ketone, will be effective in 30 minutes.

As shown above one mole of a carbonyl compound, such as acetone, reacts with a mole of caroate to produce a dioxirane, i.e. dimethyl dioxirane in the case of acetone. Theoretically, stoichiometric ratios of reactants are satisfactory in most situations. However, for purposes of this invention it is thought sufficient to provide mole ratios of between about 0.01:1 to 10:1, and preferably between about 0.1:1 to 3:1, of caroate to carbonyl containing compound. The lower caroate ratios are sufficient to provide enough dioxirane or carbonyl/caroate to sustain biocidal activity when at least about 1% by weight of each of the caroate and ketone or aldehyde are present in the composition. However, the breadth of the invention is to be construed only by functionality. Therefore, ratios of caroate to carbonyl even higher than 10:1 can be utilized is warranted. As shown in Formula 2, the oxidation of disulfide bonds requires a considerable amount of oxygen. In such instances, a dioxirane may be reduced back to its carbonyl precursor. An excess of caroate would in situ generate additional dioxirane and allow the carbonyl precursor to be oxidized and reduced on a repetitive basis for as long as necessary.

The concentration of caroate/carbonyl or dioxirane in a fluid can be as high as saturation or as low as 1% by weight. Higher concentrations require less time but are more toxic and may require special handling and removal from the matter being treated. Lower concentration will require more time to disinfect and/or sterilize the matter being treated but may require no removal. Obviously, the higher the concentration of active ingredients, the greater the chance will be that the biocide will come in contact with the organism to be destroyed. The invention is drawn to the use of the compositions for their intended purpose and the concentrations to be utilized can readily be determined by one having ordinary skill in the art. Generally, concentrations of between about 1 and 40% by weight are satisfactory.

EXAMPLES

In testing the efficacy of dioxiranes as sterilants and disinfectants, test solutions were prepared by combining caroate and a ketone in situ to produce active caroate/carbonyl compound or dioxirane-containing solutions. Test solutions containing a variable percent by weight of caroate and a ketone in distilled water were mixed at room temperature. The mixtures were clear, colorless, without evidence of gas evolution, and did not form a precipitate. Control solutions and buffer solutions were also prepared and tested concurrently.

Solutions were prepared as follows. Caroate was weighed in a tared 5 ml vial and the ketone was weighed in a 30 ml screw-cap vial. Water or buffer solution was added to the vial containing the ketone to make 10 g samples (net weight). The solutions were activated by adding the pre-weighed caroate to the aqueous ingredients in the 30 ml vial at room temperature, agitating the resulting mixture, and allowing the sample to stand for 10 minutes at room temperature. The solutions were then tested for biocidal activity.

The caroate was obtained from Aldrich Chemical Co., Inc. (Milwaukee, Wis.), marketed under the DuPont trademark "OXONE." This formulation of caroate is a mixture of potassium peroxymonosulfate, potassium hydrogen sulfate, and potassium sulfate ($2KHSO_5.KHSO_4.K_2SO_4$). Also obtained from Aldrich Chemical Co., Inc. were 10-camphorsulfonic acid and 4-hydroxy-4-methyl-2-pentanone, while acetone was obtained from Mallinckrodt Inc. (St. Louis, Mo.). Deionized, distilled water was used in all cases except where a buffer is indicated. The buffer solution was 0.5M $KH_2PO_4$, pH 7.4. The surfactants polyethylene glycol (Union Carbide, Danbury, Conn.) and nonyl phenol (Emery Industries, Los Angeles, Calif.) were tested to determine possible improvement in the antibacterial activity of the biocidal solutions due to surface action on the cells. All amounts of ingredients in the solutions are expressed in the following examples in terms of percent by weight.

Example 1

The procedure used for testing the sporicidal activity of the caroate/ketone or dioxirane compounds was according to *Official Methods of Analysis of the Association of Official Analytical Chemists* 966.04 (AOAC 1990), which is hereby incorporated by reference. *B. subtilis* (ATCC 19659) was propagated in soil extract nutrient broth. This medium was prepared by extracting 1 pound of garden soil in 1 liter of water, filtering several times through SS #588 paper, and diluting to volume. To this were added 5 g of beef extract, 5 g of NaCl, and 10 g peptone. The medium was then boiled for 20 minutes and diluted to volume. The pH was adjusted to pH 6.9 by addition of 1N NaOH, and the medium was again filtered through paper. The medium was then dispensed into tubes and autoclaved at 121° C. for 60 minutes. Tubes of soil nutrient broth were inoculated with *B. subtilis* and incubated at least 72 hours at 37° C. The culture was macerated by vortexing or grinding to break up the pellicle. The culture was then filtered through moist cotton or gauze into sterile 25×150 mm test tubes. Silk suture loops were contaminated with *Bacillus subtilis* by placing them in the culture tubes and soaking them with agitation for 10 to 15 minutes. The contaminated suture loops were then blotted on filter paper and placed in a vacuum desiccator containing CaCl$_2$ and dried for 24 hours under a vacuum of 22 inches of mercury. Contaminated loops were placed in the caroate/ketone or dioxirane solution. Each sample solution was tested with six suture loops. The suture loops were removed from the solutions 10, 20, and 30 minutes after initial exposure to the solution. The suture loops were then placed in individual tubes containing 20 to 25 ml of thioglycollate medium (Difco), the tubes were vortexed, and the suture loops were transferred to fresh tubes of thioglycollate medium.

The tubes containing thioglycollate medium were transported to an independent laboratory and were incubated at 35°±2° C. for 72 hours and then read by qualified laboratory technicians for bacterial growth.

Table 1 shows the effects of concentration of caroate and ketone and the presence of a buffer and/or surfactant on bactericidal activity on a spore-forming bacterium, *Bacillus subtilis*. Samples A-10 and B-26 show that the reaction resulting from a mixture of acetone and caroate, i.e. dimethyldioxirane, is effective in killing spore-forming bacteria. Even at low concentrations (sample B-29), the dimethyldioxirane formulation showed significant sporicidal activity. However, addition of buffer inhibited the bactericidal activity of the mixture, and caroate alone does not exhibit good antibacterial activity.

TABLE 1

| Sample | Caroate/ Acetone[1] | % Caroate + Acetone[2] | Diluent | % Surf[3] | % Growth[4] |
|---|---|---|---|---|---|
| A-1 | ND[5] | 5 | H$_2$O | 0 | 75 |
| A-5 | ND | 5 | Buffer[6] | 0.1 | 75 |
| A-10 | 0.09 | 10 | H$_2$O | 0 | 0 |
| B-24 | 0.094 | 10 | Buffer | 0 | 92 |
| B-26 | 0.047 | 15 | H$_2$O | 0 | 0 |
| B-27 | ND | 5 | H$_2$O | 0.1 | 92 |
| B-28 | 0.094 | 10 | H$_2$O | 0.1 | 33 |
| B-29 | 0.024 | 12.5 | H$_2$O | 0.1 | 25 |
| B-30 | 0.047 | 15 | Buffer | 0 | 25 |

[1]Molar ratio.
[2]Percent by weight of caroate plus acetone in the solution.
[3]Surf indicates the surfactant nonyl phenol.
[4]Growth was calculated based on any positive results taken at 10, 20, or 30 minutes of exposure.
[5]Not defined because no acetone was added.
[6]Buffer indicates 0.5 M KH$_2$PO$_4$, pH 7.4.

Example 2

The procedure of Example 1 was followed except that the ketone reactants tested were acetone (AC), camphorsulfonic acid (CSA), and 4-hydroxy-4-methyl-2-pentanone (4HP). Neither CSA nor HP demonstrated any sporicidal activity absent the presence of caroate (samples C02A and C03A, respectively). However, mixing caroate with CSA (sample C-02) or caroate with 4HP (sample C-08) in the presence of a small amount of buffer yielded no bacterial growth. A higher concentration of buffer in the mixture inhibited the sporicidal activity of caroate and CSA (sample E-07). Isopropyl alcohol (50% IPA, sample E-08) had no effect on spore growth. Therefore, the resultant dioxiranes produced by in situ mixing of caroate and either acetone, CSA, or 4HP showed 100% effectiveness in killing the spore forming bacterium, *B. subtilis*.

TABLE 2

| Sample | Caroate/ Ketone[1] | % Caroate + Ketone[2] | % Buffer[3] | % H$_2$O | % Growth[4] |
|---|---|---|---|---|---|
| C-02 | 0.38 CSA | 20 | 1 | 79 | 0 |
| C-02A | 0 CSA | 10 | 1 | 79 | 100 |
| C-03 | 0.19 4HP | 20 | 1 | 79 | 0 |

TABLE 2-continued

| Sample | Caroate/ Ketone[1] | % Caroate + Ketone[2] | % Buffer[3] | % H$_2$O | % Growth[4] |
|---|---|---|---|---|---|
| C-03A | 0 4HP | 10 | 1 | 79 | 100 |
| C-06 | 0.094 AC | 20 | 0 | 80 | 0 |
| E-07 | 0.38 CSA | 20 | 80 | 0 | 16 |
| E-08 | ND[5] | 0 | 50 IPA | 50 | 100 |

[1]Molar ratio followed by an abbreviation to indicate the ketone used.
[2]Percent by weight of caroate plus ketone in the solution.
[3]Buffer, if present, was either 0.5 M KH$_2$PO$_4$, pH 7.4, or 50% isopropyl alcohol (IPA).
[4]Growth was calculated based on any positive results taken at 10, 20, or 30 minutes of exposure.
[5]Not defined because no ketone was added.

Example 3

In this example, the procedure of Example 1 was followed with the exception that the samples were tested immediately after preparation. Table 3 shows that the combination of caroate and 4HP was completely effective in eliminating bacterial growth, whereas the combination of caroate and CSA was not as effective as after 10 minutes of incubation (Example 2). This incubation period required for caroate and CSA indicates that a reaction product is formed as the active ingredient, i.e. the dioxirane of CSA. It is also believed that 4HP and caroate also react but that the kinetics of the reaction allow the dioxirane to be formed much more rapidly. The effect of buffer in diminishing the effectiveness of the caroate-ketone combination, noted in Examples 1 and 2, was shown to be repeatable.

TABLE 3

| Sample | Caroate/ Ketone[1] | % Caroate + Ketone[2] | % H$_2$O | % Buffer[3] | % Growth[4] |
|---|---|---|---|---|---|
| C-10 | 0.38 CSA | 20 | 80 | 0 | 10 |
| C-11 | 0.38 CSA | 20 | 53 | 0 | 15 |
| C-12 | 0.38 CSA | 20 | 60 | 20 | 5 |
| C-13 | 0.19 4HP | 20 | 80 | 0 | 0 |
| C-14 | 0.19 4HP | 20 | 0 | 80 | 5 |

[1]Molar ratio followed by an abbreviation to indicate the ketone used.
[2]Percent by weight of caroate plus ketone used in the solution.
[3]Buffer indicates 0.5 M KH$_2$PO$_4$, pH 7.4.
[4]Growth was calculated based on any positive results taken at 10, 20, or 30 minutes of exposure.

Example 4

In this example, the procedure according to Example 1 was followed, including the 10 minute reaction period after mixing of the ketone and caroate. The results shown in Table 4 demonstrate that monobasic potassium phosphate buffer interferes with bactericidal and sporicidal activity (sample C-14A). A commercially available buffer used in sample C-15N did not interfere with the activity of the dioxirane containing reaction product.

TABLE 4

| Sample | Caroate/ Ketone[1] | % Caroate + Ketone[2] | Diluent | % Growth[3] |
|---|---|---|---|---|
| C-10A | 0.38 CSA | 20 | H$_2$O | 0 |
| C-11A | 0.38 CSA | 20 | 14% QAMOH[4] | 0 |
| C-13A | 0.19 4HP | 20 | H$_2$O | 0 |
| C-14A | 0.38 CSA | 20 | 0.5 M KH$_2$PO$_4$, pH 7.4 | 5 |
| C-15N | 0.38 CSA | 20 | PH-4 Fisher Buf | 0 |

TABLE 4-continued

| Sample | Caroate/ Ketone[1] | % Caroate + Ketone[2] | Diluent | % Growth[3] |
|---|---|---|---|---|
| | | | Sol[5] | |

[1]Molar ratio followed by an abbreviation indicating the ketone used in the disinfectant solution.
[2]Percent by weight of caroate plus ketone in the solution.
[3]Growth was calculated based on any positive results taken at 10, 20, or 30 minute exposures.
[4]QAMOH indicates tetrabutylammonium hydroxide.
[5]Potassium biphthalate, pH 4.0 at 25° C., supplied by Fisher (#SO-B-101).

Example 5

In this example, the procedure of Example 1 was followed with the exception that the disinfectant solutions were also tested against *Clostridium sporogenes* (ATCC 3584). *C. sporogenes* was propagated in soil extract egg-meat medium. This medium was prepared by placing 1.5 g of dehydrated egg meat medium and 15 ml of garden soil extract in 25×150 mm tubes. The medium was then autoclaved at 121° C. for 60 minutes and used to propagate the bacteria. The culture tubes were inoculated with bacteria and incubated at least 72 hours at 37° C. The culture was then filtered through moist cotton or gauze into sterile 25×150 mm culture tubes. Ten suture loops were placed in the culture, incubated, dried, and tested as described in Example 1 except that no specific instruction was given the laboratory technician to wait 10 minutes after preparing the disinfectant solution before using it.

TABLE 5

| Sample | Caroate/ Ketone[1] | % Caroate + Ketone[2] | % H$_2$O | B. subtilis[3] 10 | 20 | 30 | C. sporogenes[3] 10 | 20 | 30 |
|---|---|---|---|---|---|---|---|---|---|
| B1 | 0.38 CSA | 20 | 80 | 50 | 0 | 0 | 25 | 0 | 0 |
| CC0 | ND[4] | 10 | 90 | 100 | 100 | 100 | 100 | 100 | 100 |
| CCP | 0.14 P[5] | 20 | 80 | 0 | 0 | 0 | 0 | 0 | 0 |
| P2 | 0.19 4HP | 20 | 80 | 10 | 0 | 0 | 10 | 0 | 0 |
| CS13 | 0.38 CSA | 20 | 80 | 0 | 0 | 0 | 0 | 0 | 0 |
| CS14 | 0.38 CSA | 14 | 86 | 5 | 0 | 0 | 15 | 5 | 0 |
| CS15 | 0.38 CSA | 20 | 80 | 5 | 0 | 0 | 0 | 0 | 0 |
| CS13A | ND | 10 | 90 | 100 | 100 | 100 | 100 | 100 | 100 |

[1]Molar ratio followed by an abbreviation to indicate the ketone used.
[2]Percent by weight of caroate plus ketone in the solution.
[3]Growth of organisms was determined after 10, 20, and 30 minutes of exposure to the disinfectant solution.
[4]Not defined because no ketone was added.
[5]Indicates 2-pentanone was the ketone used.

This series of samples were run to see if the previous results were reproducible. In fact, the results are substantially the same as before. Spores are eliminated in 20 minutes, except where the caroate/CSA level was reduced to 7% each (CS14). The solutions were used immediately after mixing (no specific waiting time was specified in the protocol).

Example 6

In this example, the procedure of Example 1 was followed with the exception that the non-spore-forming bacteria *Pseudomonas aeruginosa*, *Salmonella choloraesuis*, and *Staphylococcus aureus* were used in place of *B. subtilis*. Samples (50 g) were exposed to the disinfectant solution for 20 minutes.

TABLE 6

| 50 g Samples 20-Min/Exp Stainless Steel Penicylinders | % Growth Dioxirane[1] | abcoCIDE[2] |
|---|---|---|
| P. aeruginosa | 0 | 0 |
| S. choloraesuis | 0 | 0 |
| S. aureus | 0 | 0 |

[1]Dioxirane solution contained 10% caroate, 10% CSA, and 80% H$_2$O. The molar ratio of caroate to ketone was 0.38.
[2]abcoCIDE is an activated dialdehyde solution (2% glutaraldehyde) supplied by abco Dealers, Inc., Milwaukee, WI.

This study testing against *Pseudomonas aeruginosa*, *Salmonella choloraesuis*, and *Staphylococcus aureus* with a comparison to abcoCIDE showed equivalent results in 20-minutes; both agents prevented growth in all the organisms.

Example 7

In this example, the procedure of Example 5 was followed except that the disinfectant solutions were allowed to stand for 10 minutes at room temperature before they were tested. The resulting dioxirane containing solution contained 10% caroate and either 10% CSA or 10% of the sodium salt of CSA (NaCSA). Thus, the molar ratio of caroate to ketone was 0.38 in each case. NaCSA was prepared by adding 0.172 g of NaOH per gram of CSA in solution. The appropriate amount of caroate was then added to the solution to prepare the dioxirane for testing. As shown in Table 7, the sodium salt of CSA (sample 2CNA1-9) reduces the effectiveness of the dioxirane against *B. subtills*. This result suggests that the presence of ions in the buffered solutions may interfere with the effectiveness of the dioxiranes in those test as well. However, longer exposure times to NaCSA-containing dioxirane solutions yielded increased sporicidal activity over shorter exposures. Table 7 also shows that NaCSA was 100% effective in killing *C. sporogenes*. Dioxirane solutions prepared from CSA and caroate were excellent bactericides against both *B. subtilis* and *C. sporogenes*. Each datum is the average of 9 repetitions of the experiment.

TABLE 7

| Sample | Ketone | B. subtilis 10 min | 20 min | 30 min | C. sporogenes 10 min | 20 min | 30 min |
|---|---|---|---|---|---|---|---|
| 2CNA1-9 | NaCSA | 97 | 67 | 19 | 0 | 0 | 0 |
| 2CS1-9 | CSA | 0 | 0 | 0 | 0 | 0 | 0 |

Example 8

In this example, the procedures of Example 5 were followed including that no specific instructions were given to the lab technician to wait 10 minutes prior to use of the solution. The resulting dioxirane containing solutions were tested for bactericidal activity, then the dioxirane containing solutions were stored at 20° to 24° C. for 6 days and retested. The results of the tests immediately after bringing together the caroate and ketones are shown in Table 8. A wide range of results were obtained in the first 10 minutes, suggesting that the initial 10 minutes after mixing the caroate and ketone are critical. This time period allows the reaction to occur which results in generation of the dioxirane. Twenty minutes after preparation of the dioxirane solution, however, the sporicidal activity of the test solutions was established.

tures were prepared, TS-1, TS-2, and TS-3, each containing equimolar ratios of caroate and CSA, i.e. 26% w. caroate and 10% w. CSA. The three test mixtures were then tested against both *B. subtilis* and *C. sporogenes*. Analyses of culture tubes were made 3, 7, 14, and 21 days after beginning the experiment. As shown in Table 10, no growth was detected in any tubes for either organism. The same three test mixtures were kept at room temperature for 2 days and then the effectiveness of the test mixtures was tested again in the same manner. As shown in Table 10A, no growth of either organism was observed at any time point. These results show that the dioxirane of CSA remained effective against spore-forming bacteria for at least 2 days.

TABLE 8

| Sample | Formula Caroate/ CSA[2] | % Caroate + Ketone[3] | *B. subtilis*[1] % Growth (min/exp) 10 | 20 | 30 | *C. sporogenes*[1] % Growth (min/exp) 10 | 20 | 30 |
|---|---|---|---|---|---|---|---|---|
| 8-1-PC | 0.38 | 20 | 25 | 0 | 0 | 50 | 0 | 0 |
| 8-1A-PC | 0.38 | 20 | 100 | 0 | 0 | 50 | 0 | 0 |
| 8-2-PC | 0.31 | 22 | 0 | 0 | 0 | 0 | 0 | 0 |
| 8-2A-PC | 0.31 | 22 | 25 | 0 | 0 | 0 | 0 | 0 |
| 8-3-PC | 0.25 | 25 | 0 | 0 | 0 | 0 | 0 | 0 |
| 8-3A-PC | 0.25 | 25 | 0 | 0 | 0 | 0 | 0 | 0 |
| 8-4-PC | 0.38 | 24 | 75 | 0 | 0 | 0 | 0 | 0 |
| 8-4A-PC | 0.38 | 24 | 25 | 0 | 0 | 0 | 0 | 0 |
| 8-5-PC | 0.38 | 30 | 0 | 0 | 0 | 0 | 0 | 0 |
| 8-5A-PC | 0.38 | 30 | 50 | 0 | 0 | 25 | 0 | 0 |
| 8-6-PC | 0.14 P[4] | 20 | 0 | 0 | 0 | 25 | 0 | 0 |
| 8-6A-PC | 0.12 P | 22 | 0 | 0 | 0 | 25 | 0 | 0 |
| 8-7-PC | ND[5] | 10 | 100 | 100 | 100 | 50 | 0 | 0 |
| 8-7A-PC | 0 | 10 | 100 | 100 | 100 | 100 | 100 | 100 |

[1]Growth was determined after 10, 20, and 30 minutes of exposure of the organisms to the disinfectant solutions.
[2]Molar ratio.
[3]Percent by weight of caroate plus ketone in the solution.
[4]P indicates 2-pentanone was substituted for CSA.
[5]Not defined because no ketone was added.

Example 9

Table 9 shows the results of testing the dioxirane solutions selected from samples from Table 8 after 6 days of storage at 20 to 24° C. Dioxiranes prepared with 10% caroate and 10% CSA gave almost the same results as when freshly prepared, 100% sporicidal activity after a 20 minute exposure. However, dioxiranes prepared with caroate and pentanone (sample 8-6-PC) exhibited no sporicidal activity 6 days after preparation. Thus, in terms of long-term stability, dioxiranes prepared with camphorsulfonic acid yield the best results of those tested.

TABLE 9

| Sample | Formula Caroate/ CSA[2] | % Caroate + Ketone[3] | *B. subtilis*[1] % Growth (min/exp) 10 | 20 | 30 | *C. sporogenes*[1] % Growth (min/exp) 10 | 20 | 30 |
|---|---|---|---|---|---|---|---|---|
| 8-1-PC | 0.38 | 20 | 50 | 0 | 0 | 0 | 0 | 0 |
| 8-2-PC | 0.31 | 22 | 50 | 0 | 0 | 0 | 0 | 0 |
| 8-3-PC | 0.25 | 25 | 25 | 0 | 0 | 0 | 0 | 0 |
| 8-4-PC | 0.38 | 24 | 25 | 0 | 0 | 25 | 0 | 0 |
| 8-5-PC | 0.38 | 30 | 25 | 0 | 0 | 0 | 0 | 0 |
| 8-6-PC | 0.14 P[4] | 20 | 100 | 100 | 100 | 100 | 100 | 100 |

[1]Growth was determined after 10, 20, and 30 minutes of exposure to the disinfectant solutions.
[2]Molar ratio.
[3]Indicates the percent by weight of the caroate and ketone.
[4]P indicates 2-pentanone was substituted for CSA.

Example 10

In this example, the procedure of Example 5 was followed with the exception that the mixture of caroate and CSA was equilibrated for 10 minutes to form the dioxirane of CSA before being tested. Three test mix-

TABLE 10

| Sample | Microbe | % Growth 3 d | 7 d | 14 d | 21 d |
|---|---|---|---|---|---|
| TS-1 | *B. subtilis* | 0 | 0 | 0 | 0 |
|  | *C. sporogenes* | 0 | 0 | 0 | 0 |
| TS-2 | *B. subtilis* | 0 | 0 | 0 | 0 |
|  | *C. sporogenes* | 0 | 0 | 0 | 0 |
| TS-3 | *B. subtilis* | 0 | 0 | 0 | 0 |
|  | *C. sporogenes* | 0 | 0 | 0 | 0 |

TABLE 10A

| Sample | Microbe | % Growth 3 d | 7 d | 14 d | 21 d |
|---|---|---|---|---|---|
| TS-1 | *B. subtilis* | 0 | 0 | 0 | 0 |
|  | *C. sporogenes* | 0 | 0 | 0 | 0 |
| TS-2 | *B. subtilis* | 0 | 0 | 0 | 0 |
|  | *C. sporogenes* | 0 | 0 | 0 | 0 |
| TS-3 | *B. subtilis* | 0 | 0 | 0 | 0 |

TABLE 10A-continued

| Sample | Microbe | % Growth | | | |
|---|---|---|---|---|---|
| | | 3 d | 7 d | 14 d | 21 d |
| | C. sporogenes | 0 | 0 | 0 | 0 |

Example 11

The procedure used for testing the tuberculocidal activity of the caroate/ketone or dioxirane compounds was the Tuberculocidal Activity Test Method adopted by the Environmental Protection Agency on Dec. 11, 1985, which is hereby incorporated by reference. See u.s. Environmental Protection Agency, Office of Pesticides and Toxic Substances, Data Call-In Notice for Tuberculocidal Effectiveness Data for All Antimicrobial Pesticides with Tuberculocidal Claims (Received Jun. 13, 1986). Test solutions were evaluated using *Mycobacterium boris* BCG (TMC 1028) grown to a titer of $1.49 \times 10^7$ colony forming units (CFU) per ml of modified Proskauer-Beck medium containing Tween 80. This medium contains 2.5 g $KH_2PO_4$, 5.0 g asparagine, 0.6 g $MgSO_4.7H_2O$, 2.5 g magnesium citrate, 0.0046 g $FeCl_3$, 0.001 g $ZnSO_4.7H_2O$, 20 ml glycerol, and 1 ml Tween 80 per liter. Aliquots were stored at $-70°$ C. until use. Aliquots were thawed at room temperature, diluted with an equal volume of buffered gelatin, and briefly homogenized in an ice bath. Buffered gelatin contains 33 ml of solution A (2.8 g $NaH_2PO_4$/100 ml water), 67 ml of solution B (5.4 g $Na_2HPO_4.7H_2O$/100 ml water), 2 g Bacto-gelatin (Difco), and water to raise the volume to 200 ml. The cell suspension was then diluted to about $10^7$ CFU/ml in saline-tween (0.85% NaCl, 0.1% (v/v) Tween 80) containing 5% calf serum. Then, 9 ml aliquots of the disinfectant to be tested were equilibrated at 20° C. and 1 ml of the *M. bovis* culture was added and mixed by vortexing. At each time interval, a 1 ml aliquot was removed and mixed with 50 ml of neutralizer broth (30 g soybean casein digest broth, 5 g Tween 80, 0.7 g azolectin, and 0.5 g sodium thiosulfate per liter of water). This suspension was then filtered through a hydrophobic edge 0.45 mm membrane. The membrane was rinsed thoroughly with 50 ml of saline (0.85% NaCl) and then placed on Mycobacteria 7H11 agar and incubated in a humidification chamber for 21 days at 37° C. Mycobacteria 7H11 agar contains: 1 g pancreatic digest of casein, 0.5 g L-glutamic acid, 0.4 g sodium citrate, 0,001 g pyroxidine, 0.0005 g biotin, 0.04 g ferric ammonium sulfate, 0.5 g ammonium sulfate, 1.5 g disodium phosphate, 1.5 g monopotassium phosphate, 0.05 g magnesium sulfate, 15 g Bacto-agar, 0.001 g Bacto malachite green, 5 ml glycerol per liter. After sterilizing, the medium is cooled to 50°–55° C. and 100 ml of Bacto Middlebrook OADC enrichment is added.

Table 11 shows the results of exposure to a resulting solution of the dioxirane of CSA containing 10% caroate, 10% CSA, and 80% $H_2O$. The molar ratio of caroate to CSA was 0.38. The dioxirane disinfectant produced in this manner yielded $\leq 1$ 15 survivor of *M. bovis* BCG after 20 minutes of exposure.

TABLE 11

| Exposure Time (minutes) | Colony Forming Units (CFU) (replicates) | | | |
|---|---|---|---|---|
| | 1 | 2 | 3 | 4 |
| 10 | 1 | 3 | 3 | 4 |
| 20 | 1 | 1 | * | 1 |
| 30 | 0 | 0 | 0 | 0 |
| 60 | 0 | 0 | 0 | 0 |
| 120 | 0 | 0 | 0 | 0 |

*Contaminated Plate.

Example 12

The procedure used for testing the fungicidal activity of caroate/ketone or dioxirane compounds was the Fungicidal Activity Test as described in 1 AOAC Methods, chapter 6, 955.17 (15th ed. 1990), which is hereby incorporated by reference. In brief, a stock culture of *Trichophyton mentagrophytes* (ATCC 9533) was inoculated onto neopeptone-glucose agar (NGA) slants and incubated at 25° to 30° C. for 10 days. NGA consists of 10 g neopeptone, 20 g glucose, and 20 g agar per liter of water. The culture was then transferred from the slant to 5 NGA plates and incubated at 25° to 30° C. for 10 days. After incubation, the mycelial mats were removed using a sterile spatula. The culture was macerated in 25 ml of saline by vortexing it with glass beads. The suspension was filtered through sterile cotton gauze to remove the hyphal elements. The conidial titer was determined with a hemacytometer and the titer was adjusted to approximately $10^6$ conidia per ml.

The disinfectant solution was prepared by mixing the powder with the liquid and letting it dissolve for ten minutes. Five ml of the disinfectant solution was added to each of 10 tubes and equilibrated at 20° C. in a water bath. Once every 30 seconds, a 0.5 ml aliquot of the conidial suspension was added to each tube of disinfectant. After 5, 10, 20, and 30 minutes of exposure, a 4 mm loop was used to remove a sample from each assay tube. This sample was transferred to a tube of neopeptone-glucose broth with neutralizers (NGB/N; 10 g neopeptone, 20 g glucose, 0.5 g sodium thiosulfate per liter of water). These tubes were incubated at 25° to 30° C. for 10 days.

A 5% stock solution of phenol was further diluted to make 1:60 and 1:70 dilutions. Five ml of the diluted phenol was added to each of 10 tubes and equilibrated at 20° C. in a water bath. Once every 30 seconds, a 0.5 ml aliquot of the conidial suspension was added to each tube of phenol. After 5, 10, 20, and 30 minutes of exposure, a 4 mm loop was used to remove a sample from each assay tube for transfer to a tube of NGB/N. These broth tubes were then incubated at 25° to 30° C. for 10 days.

Following incubation, each tube was examined for growth of the fungus and tubes were scored as positive or negative. Neutralization was tested by inoculating a series of tubes that were scored as negative with 10 to 100 CFU of the challenge organism. These tubes were incubated for 10 days at 25° to 30° C. and then observed and scored.

Table 12 shows that *Trichophyton mentagrophytes* is effectively killed by a five minute exposure to a solution of the dioxirane of CSA containing 10% CSA, 10% caroate, and 80% water. The molar ratio of caroate to CSA was 0.38. The fungus was resistant to phenol at the concentrations tested and positive growth was observed in the neutralization tests, demonstrating effective neutralization of the dioxirane solutions.

TABLE 12

| Exposure Time (minutes) | Results |
| --- | --- |
| 5 | 0/10[1] |
| 10 | 0/10 |
| 20 | 0/10 |
| 30 | 0/10 |

[1] Number of tubes with growth of *T. mentagrophytes*/Total number of tubes.

Example 13

The procedure for testing the virucidal efficacy of caroate/ketone or dioxirane containing solutions was carried out according to the guidelines given by the Environmental Protection Agency for virucidal preparations, U.S. Environmental Protection Agency, "Efficacy Data Requirements: Virucide" (Office of Pesticide Programs, EPA, 1976), which is hereby incorporated by reference.

Briefly, a confluent flask of human epithelioid cervical carcinoma cells (HeLa) was inoculated with 2 ml of poliovirus type 1 in minimum essential medium (MEM) with 2% calf serum at a multiplicity of infection of 0.01. The virus was allowed to absorb for 30 minutes, then approximately 10 ml of medium was added to the flask. The flask was incubated at 37° C. with 5% $CO_2$ until it reached 4+ cytopathic effect (CPE). The flask was then frozen at $-70°$ C. and thawed to harvest the virus. The virus stock was stored at $-70°$ C.

The TCID-50 assay was performed as follows. First, 96-well microtiter plates were seeded with HeLa cells. The plates were incubated overnight at 37° C. in 5% $CO_2$ until they reached confluence. Serial 1/10 dilutions were made of the virus in MEM with 2% calf serum. The dilutions were added to the wells on the plates in 0.1 ml aliquots in quadruplicate. Four wells, included as negative controls, received only MEM with 2% calf serum. The virus was allowed to absorb to the cells for 30 minutes, then an additional 0.1 ml of MEM with 2% calf serum was added to each well on the plates. The plates were incubated at 37° C. with 5% $CO_2$ for 3 days. The plates were then fixed with 10% formalin and stained with 0.1% crystal violet. The TCID-50 of the sample was determined using the Reed-Muench method.

Toxicity controls were performed as follows. Ten ml aliquots of the disinfectant solution were placed in sterile tubes in a 20° C. water bath and allowed to equilibrate for 10–15 minutes. A sterile carrier was placed in each tube for 15 minutes (the maximum exposure time) then removed and vortexed in 3 ml MEM with 2% calf serum. Serial 1/10 dilutions were made of the media containing the carriers. The dilutions were placed on HeLa cells in a 96-well plate as in the TCID-50 procedure. MEM with 2% calf serum was added to four wells as cell controls. The plates were incubated at 37° C. for 30 minutes, than an additional 0.1 ml of MEM with 2% calf serum was added to each well on the plates. The plates were incubated at 37° C. with 5% $CO_2$ for 3 days. The plates were then fixed with 10% formalin and stained with 0.1% crystal violet. Each well was scored for toxicity and the TCID-50 was calculated using the Reed-Muench method if toxicity was detected.

Neutralization controls were performed as follows. Ten ml aliquots of the disinfectant solutions were placed in sterile tubes in a water bath and allowed to equilibrate for 10–15 minutes at 20° C. A sterile carrier was placed in each tube for 15 minutes (the maximum exposure time) then removed and vortexed in 3 ml MEM with 2% calf serum. Serial 1/10 dilutions were made of the media containing the carriers. Each dilution was inoculated with virus to create a final concentration of 10 to 100 virus per ml. A blank containing MEM with 2% calf serum was also inoculated with virus as a virus control. The dilutions were placed on HeLa cells in a 96-well plate as in the TCID-50 procedure. The plates were incubated at 37° C. for 30 minutes, then 0.1 ml of MEM with 2% calf serum was added to each well on the plates. The plates were incubated at 37° C. with 5% $CO_2$ for 3 days. The plates were then fixed with 10% formalin and stained with 0.1% crystal violet. Each well was scored for CPE.

A caroate/ketone or dioxirane disinfectant solution was prepared by mixing 3 g of caroate with 27 g of deionized distilled water containing 3 g of CSA. Exposure of the carriers to the disinfectant solutions was begun by placing carriers in stock virus for 15 minutes, then removing them and allowing them to dry for 15 minutes at room temperature on sterile filter paper. Ten ml aliquots of the disinfectants were placed in sterile tubes and equilibrated at 20° C. in a water bath. Contaminated carriers were placed in the tubes for 5, 10, or 15 minutes, then removed and vortexed in 3 ml MEM with 2% calf serum to neutralize the disinfectant and release the virus. Each exposure time was tested with three replicates. The TCID-50 procedure was performed on the media containing the carriers to assay for the virus. Three contaminated carriers were vortexed in 3 ml aliquots of MEM with 2% calf serum and ritered as positive virus controls.

Table 13 shows the results of the dioxirane of CSA disinfectant in reducing the virus titer in disinfectant efficacy trials. A three $\log_{10}$ reduction is required by the EPA for a virucidal preparation. When no virus is detected after exposure to the disinfectant, the $\log_{10}$ reduction of the virus by the disinfectant is calculated by subtracting the TCID-50 (the detectable limit) from the average virus control titer. The disinfectant reduced the virus titer 3.4 $\log_{10}$, thus meeting the requirements for a virucidal preparation by the EPA. Toxicity control experiments showed that the first dilution of the carrier in 3 ml of MEM with 2% CS (carrier/3 ml or 1/3 dilution) was toxic to the cells in three of the four determinations. A 1/10 dilution of the medium containing the carrier was not toxic. The TCID-50 for both lots of the dioxirane of CSA solution was $10^{1.3}$/ml. Neutralization control experiments showed that the first dilution of the carrier in 3 ml of MEM with 2% CS (1/3 dilution) as toxic, therefore the virus could not be detected. A 1/10 dilution of the medium containing the carrier was sufficient to neutralize the dioxirane solution. Viral cytopathic effects (CPE) comparable with the virus controls were detected in four determinations.

TABLE 13

| Exposure Time | TCID-50 | Log Reduction |
| --- | --- | --- |
| Virus Control | $10^{4.7}$/mL | — |
| 5 Min | $10^{1.3}$/mL | >3.4 |
| 10 Min | $10^{1.3}$/mL | >3.4 |
| 15 Min | $10^{1.3}$/mL | >3.4 |

While certain representative embodiments of the invention have been described herein for the purposes of illustration, the invention may be embodied in other specific forms without departing from its spirit or essential characteristics, and the described examples should not be considered restrictive, but only illustrative. The scope of the invention is therefore defined by the appended claims and their equivalents, rather than by the foregoing examples.

We claim:

1. A method for the disinfection and sterilization of material contaminated with one or more members selected from the group consisting of bacteria, bacterial spores, fungi and viruses, comprising the steps of:
   (a) providing a biocidal fluid containing a mixture of peroxymonosulfate and a ketone and reaction products thereof wherein the molar ratio of peroxymonosulfate to ketone is at least 0.01:1; and
   (b) contacting the material contaminated with one or more members selected from the group consisting of bacteria, bacterial spores, fungi and viruses with the biocidal fluid of step (a) for a time sufficient for disinfecting and sterilizing said material.

2. The method of claim 1 wherein said molar ratio of peroxymonosulfate to ketone is between about 0.01:1 and 10:1.

3. The method of claim 2 wherein said ketone is a member selected from the group consisting of acetone, 2-pentanone, 4-hydroxy-4-methyl-2-pentanone, and camphorsulfonic acid.

4. The method of claim 3 wherein said biocidal fluid is a polar solution.

5. The method of claim 4 wherein said biocidal fluid is an aqueous solution.

6. The method of claim 5 wherein said ketone is acetone.

7. The method of claim 5 wherein said ketone is 2-pentanone.

8. The method of claim 5 wherein said ketone is 4-hydroxy-4-methyl-2-pentanone.

9. The method of claim 5 wherein said ketone is camphorsulfonic acid.

10. The method of claim 5 wherein said mixture of peroxymonosulfate and a ketone and reaction products thereof is present in said aqueous solution at a concentration between about 1% by weight and saturation.

11. The method of claim 5 wherein said material contains a surface area which is to be disinfected and sterilized.

12. The method of claim 11 wherein said material is a medical instrument.

13. The method of claim 1 wherein said molar ratio of peroxymonosulfate to ketone is between about 0.1:1 and 3:1.

14. The method of claim 2 wherein said biocidal fluid further comprises at least one compound selected from the group consisting of peroxides, aldehydes, epoxides and surfactants.

15. The method of claim 1 wherein said biocidal fluid contains a dioxirane as one of said reaction products between said peroxymonosulfate and ketone.

16. The method of claim 15 wherein said molar ratio of peroxymonosulfate to ketone is between about 0.01:1 and 10:1.

17. The method of claim 16 wherein said ketone is a member selected from the group consisting of acetone, 2-pentanone, 4-hydroxy-4-methyl-2-pentanone, and camphorsulfonic acid and said dioxirane is a member selected from the group consisting of dimethyldioxirane, methyl-n-propyldioxirane, 4-hydroxy-4-methyl-2-pentadioxirane, and the dioxirane of camphorsulfonic acid.

18. The method of claim 17 wherein said biocidal fluid is a polar solution.

19. The method of claim 18 wherein said biocidal fluid is an aqueous solution.

20. The method of claim 19 wherein said ketone is acetone and said dioxirane is dimethyldioxirane.

21. The method of claim 19 wherein said ketone is 2-pentanone and said dioxirane is methyl-n-propyldioxirane.

22. The method of claim 19 wherein said ketone is 4-hydroxy-4-methyl-2-pentanone and said dioxirane is 4-hydroxy-4-methyl-2-pentadioxirane.

23. The method of claim 19 wherein said ketone is camphorsulfonic acid and said dioxirane is the dioxirane of camphorsulfonic acid.

24. The method of claim 19 wherein said mixture of peroxymonosulfate and a ketone and dioxirane reaction product is present in said aqueous solution at a concentration between about 1% by weight and saturation.

25. The method of claim 19 wherein said material contains a surface area which is to be disinfected and sterilized.

26. The method of claim 25 wherein said material is a medical instrument.

27. The method of claim 16 further comprising at least one compound selected from the group consisting of peroxides, aldehydes, epoxides and surfactants.

* * * * *